(12) United States Patent
Evans et al.

(10) Patent No.: US 6,407,231 B1
(45) Date of Patent: Jun. 18, 2002

(54) PROCESS FOR THE PREPARATION OF A MIXTURE OF ALKYLATED PHENOTHIAZINES AND DIPHENYLAMINES

(75) Inventors: Samuel Evans, Marly; Stephan Allenbach, Sisseln; Paul Dubs, Cham, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/609,960

(22) Filed: Jul. 5, 2000

(30) Foreign Application Priority Data

Jul. 9, 1999 (CH) .............................. 1280/99

(51) Int. Cl.⁷ .................. C07D 279/18; C07D 279/14; C07D 279/36
(52) U.S. Cl. ............... 544/35; 544/31; 544/36; 544/44
(58) Field of Search .............. 544/31, 35, 36, 544/44

(56) References Cited

U.S. PATENT DOCUMENTS

| | | | |
|---|---|---|---|
| 4,824,601 A | 4/1989 | Franklin | 252/401 |
| 5,413,737 A * | 5/1995 | Evans | 252/405 |
| 5,503,759 A | 4/1996 | Evans et al. | 252/47.5 |
| 5,780,681 A | 7/1998 | Eller et al. | 564/485 |
| 5,874,621 A | 2/1999 | Eller et al. | 564/445 |

FOREIGN PATENT DOCUMENTS

EP 0 810 200 12/1997

OTHER PUBLICATIONS

Hawley's Condensed Chemical Dictionary, Eleventh Edition, pp. 90–91, (1987).

Hawley's Condensed Chemical Dictionary N.I. Sax et al; pp. 90–91 Van Nostrand Reinhold Co., N.Y 1981.

* cited by examiner

Primary Examiner—Mukund J. Shah
Assistant Examiner—Sudhaker B. Patel
(74) Attorney, Agent, or Firm—Kevin T. Mansfield

(57) ABSTRACT

This invention relates to a novel, technically advantageous process for the preparation of a mixture of alkylated phenothiazines and diphenylamines. Starting from diphenylamine, this is reacted with elemental sulfur in the presence of iodine, and the substance mixture of diphenylamine and phenothiazine is treated with an olefin in the presence of an acid catalyst.

5 Claims, No Drawings

PROCESS FOR THE PREPARATION OF A MIXTURE OF ALKYLATED PHENOTHIAZINES AND DIPHENYLAMINES

The present invention relates to a novel, technically advantageous process for the preparation of a mixture of alkylated phenothiazines and diphenylamines.

Additives are added to improve the performance properties of numerous organic products having a wide range of application in the technology, e.g. lubricants, hydraulic fluids, metal working fluids, fuels or polymers.

Liquid mixtures of aminic antioxidants have been used for some time in particular in lubricating oils for combustion engines. It is known from U.S. Pat. No. 2,433,658 to prepare phenothiazine by reacting diphenylamine with sulfur. EP-A-0 475 904 describes the preparation of a substance mixture of alkylated phenothiazines by reacting alkylated diphenylamines with sulfur. The alkylated diphenylamine mixture is prepared beforehand by the process described in EP-A-0 149 422 by reacting diphenylamine with an olefin as alkylating agent, e.g. diisobutylene. This alkylation process is not very selective since mixtures with differently alkylated products are obtained, e.g. mixtures of 2,2'-, 2,4'-, 4-, 4,4'- and 2,4,4'-alkylated diphenylamines. The subsequent reaction of such mixtures by the process described in EP-A-0 475 904 yields mixtures of correspondingly alkylated diphenylamines and phenothiazines of low selectivity.

This invention has for its general object to provide mixtures of alkylated diphenylamines and phenothiazines with increased selectivity of the alkylation in 3- and 7-position. EP-A-0 659 749 describes the selective alkylation of a mixture of diphenylamines and phenothiazines with olefins, e.g. diisobutylene. However, this process is not advantageous because the synthesis requires that mixtures of diphenylamine and phenothiazine are already present as starting material.

This invention has the more restricted object of preparing—starting from pure diphenylamine or naphthylamine as sole starting material—mixtures of alkylated diphenylamines and phenothiazines having increased selectivity of the alkylation in 3- and 7-position.

This object is achieved by this invention, which relates to a so-called one-pot process for the preparation of a mixture of alkylated phenothiazines and diphenylamines.

This invention relates to a process for the preparation of a mixture comprising alkylated phenothiazines of formula:

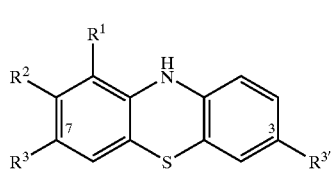
(I)

and correspondingly substituted diphenylamines of formula:

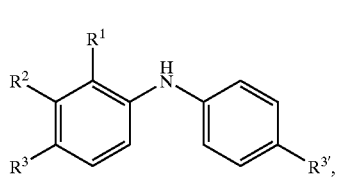
(II)

wherein $R^1$ and $R^2$ are hydrogen or together are the group:

(A)

one of $R^3$ and $R^{3'}$ is hydrogen and the other is $C_2$–$C_{30}$alkyl, cyclo-$C_5$–$C_{12}$alkyl-$C_2$–$C_4$alkyl α-$C_1$–$C_2$alkylbenzyl or α,α-dimethylbenzyl;

or both $R^3$ and $R^{3'}$ are $C_2$–$C_{30}$alkyl, cyclo-$C_5$–$C_{12}$alkyl-$C_2$–$C_4$alkyl, α-$C_1$–$C_2$akylbenzyl or α,α-dimethylbenzyl, if $R^1$ and $R^2$ are hydrogen; or $R^3$ is hydrogen and $R^{3'}$ is $C_2$–$C_{30}$alkyl, cyclo-$C_5$–$C_{12}$alkyl-$C_2$–$C_4$alkyl, α-$C_1$–$C_2$alkylbenzyl or α,α-dimethylbenzyl, if $R^1$ and $R^2$ together are the group A, which process comprises reacting a diphenylamine of formula:

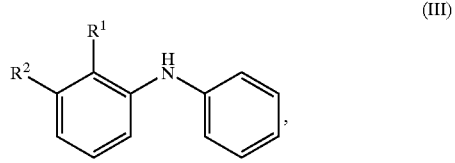
(III)

wherein $R^1$ and $R^2$ have the meanings given for formula 1, with elemental sulfur in the presence of a condensation catalyst selected from the group consisting of iodine, aluminium bromide, aluminium chloride, iron-III-chloride, antimonium chloride, copper iodide and sulfur iodide and reacting the obtainable substance mixture of diphenylamine (III) and phenothiazine of formula:

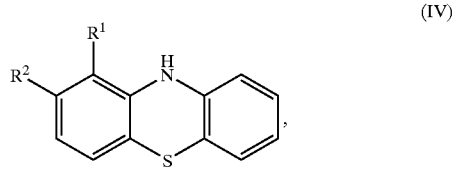
(IV)

wherein $R^1$ and $R^2$ have the meanings cited for formula I, with an olefin of formula:

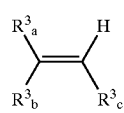
(V)

containing the number of the carbon atoms in $R^3$ or $R^{3'}$, wherein one of $R^3_a$, $R^3_b$ and $R^3_c$ is cyclo-$C_5$–$C_{12}$alkyl or phenyl and the other radicals are hydrogen or methyl, or $R^3_a$, $R^3_b$ and $R^3_c$ are each independently of one another hydrogen or $C_1$–$C_{28}$alkyl, in situ in the presence of an acid catalyst and isolating the mixture of the compounds (I) and (II).

In a particularly preferred embodiment of this invention, the two process steps are carried out as one-pot processes. $R^3$ and $R^{3'}$ defined as $C_2$–$C_{30}$alkyl are preferably $C_2$–$C_{20}$alkyl, more preferably $C_4$–$C_{12}$alkyl, e.g. straight-chain or branched (from 3 carbon atoms) alkyl, typically ethyl, n-propyl, isopropyl, n-butyl, isobutyl, tert-butyl, n-pentyl, isopentyl, neopentyl, n-hexyl, 2-ethyl-n-butyl, 1-methyl-n-pentyl, 1,3-dimethylbutyl, n-heptyl, isoheptyl, 1,1,3,3-tetramethylbutyl, 1-methylhexyl, 2-methylhexyl, n-octyl, isooctyl, 1,4,4-trimethyl-2-pentyl, 1-methylheptyl, n-nonyl, 1,1,3-tri-methylhexyl, n-decyl, n-undecyl, n-dodecyl, 1-methylundecyl, n-dodecyl, n-tetradecyl, n-hexadecyl, n-octadecyl or n-eicosyl.

Cyclo-$C_5$–$C_{12}$alkyl-$C_2$–$C_4$alkyl is, for example, cyclopentyl-1,1-ethyl, cyclohexyl-1,1-ethyl, cyclopentyl-1,2-ethyl, cyclohexyl-1,2-ethyl, cyclopentyl-1,2-propyl or cyclohexyl-1,2-propyl.

α-$C_1$–$C_2$alkylbenzyl is, for example, methylbenzyl (=1,1-phenethyl).

In a preferred embodiment of this process the reaction is carried out using about 0.5 to 200 mol % of elemental sulfur in the presence of about 0.001 to 10 mol % of the condensation catalyst selected from the group consisting of iodine, aluminium bromide, aluminium chloride, iron-III-chloride, antimonium chloride, copper iodide and sulfur iodide in the temperature range from about 80° to 250° C.

In another preferred embodiment of the process, the reaction is carried out using 10 to 150 mol %, preferably 15 to 100 mol %, of elemental sulfur.

The preferred embodiments of this process include the reaction with 0.001 to 1.0 mol % of the condensation catalyst.

In a particularly preferred embodiment of this process the reaction is carried out using 0.001 to 0.01 mol % of elemental iodine.

The reaction temperature is in the range from about 800 to 250° C., preferably from 120° to 190° C. In the course of the reaction, hydrogen sulfide ($H_2S$) is formed. Owing to its toxicity and bad smell this is removed from the reaction vessel and led into an aqueous alkali hydroxide solution. Alkali sulfide forms then which can be easily disposed of.

In the first process step, the reaction time can be e.g. from about 1 to 15 hours, a reaction time of 2 to 4 hours being useful and one of about 1 to 2 hours being preferred.

The reaction can be carried out by adding the diphenylamine (III), where appropriate dissolved in one of the cited solvents, to the sulfur and the catalyst. This mixture is heated, with stirring, to the cited temperature. The course of the reaction can be observed via the formation of hydrogen sulfide. After the cited reaction time, or if analysis no longer shows any free sulfur, the reaction of the first process step can be terminated, e.g. by cooling the reaction vessel to about 100° C.

The mixture of the compounds (III) and (IV) can be used in the second process step in a molar ratio of about 95:5 to 5:95, preferably of 30:70 to 70:30.

In a preferred variant of the process, the compounds (III) and compounds (IV) are used in the second process step in a molar ratio of about 30:70 to 5:95, particularly preferably of 20:80 to 10:90.

The olefin (V) is used in the second process step in a molar ratio of about 0.5 to 4.0 mol, preferably of 1.0 to 3.0 mol, more preferably of 1.0 to 2.0 mol, per mol of the mixtures of the compounds (III) and (IV).

The number of the carbon atoms in the olefin (V) corresponds to the number of carbon atoms in $R^3$ or $R^{3'}$. If $R^3$ or $R^{3'}$ is tert-octyl or 1,4,4-trimethyl-2-pentyl, diisobutylene is used as olefin (V). Other suitable olefins are, for example, ethylene, propylene, isobutylene, 2-methyl-pentene, tripropylene, tetrapropylene, styrene or methylstyrene.

Suitable acid catalysts are proton donors (so-called Brønsted acids), electron acceptor compounds (so-called Lewis acids), cation exchanger resins, alumosilicates or naturally occurring or modified sheet silicates.

Suitable proton donors (so-called Brønsted acids) are, for example, salt-forming inorganic or organic acids, e.g. mineral acids such as hydrochloric acid, sulfuric acid or phosphoric acid, carboxylic acids, e.g. acetic acid, or sulfonic acids, e.g. methanesulfonic acid, benzenesulfonic acid or p-toluenesulfonic acid. p-Toluenesulfonic acid is particularly suitable.

Suitable electron acceptor compounds (so-called Lewis acids) are, for example, tin tetra-chloride, zinc chloride, aluminium chloride or boron trifluoride etherate. Tin tetrachloride and aluminium chloride are particularly suitable.

Suitable cation exchanger resins are, for example, styrene-divinylbenzene copolymers containing sulfo acid groups as ion exchanger function, e.g. the known products Amberlite® and Amberlyst®, of Rohm and Haas, e.g. AMBERLITE 200, or Dowex® 50, of Dow Chemicals, perfluorinated ion exchanger resins, e.g. Nafion® H, of DuPont, or other superacid ion exchanger resins, e.g. those described by T. Yamaguchi in *Applied Catalysis* 61, 1–25 (1990), or M.Hino et al. in *J. Chem. Soc. Chemical Comm.* 1980, 851–852.

Suitable alumosilicates are, for example, amorphous aluminium silicates which contain about 10–30% of silicium dioxide and about 70–90% of aluminium oxide and which are used in petrochemistry, e.g. Aluminium Silicate HA-HPV®, of Ketjen (Akzo), or crystalline aluminium silicates, e.g. so-called zeolites, which are used as inorganic cation exchangers, as so-called molecular sieves or in the petrochemistry as so-called cracking catalysts, e.g. faujasites, of Union Carbide, e.g. Zeolith R®, Zeolith Y® and ultrastable zeolite; Zeolith Beta® and Zeolith ZSM-12®, of Mobil Oil; or Zeolith Mordenit®, of Norton.

Suitable naturally occurring sheet silicates are also called acid earths and are e.g. mont-morillonites which are activated e.g. with mineral acids such as sulfuric acid and/or hydrochloric acid and which preferably have a moisture content of less than 10%, preferably of less than 5%, for example so-called earths of the Fuller type, e.g. types commercially available under the name Fulcat®, e.g. the types 20, 22 A, 22 B and 40 (alumina activated with sulfuric acid), Fulmont® (Laporte Industries), e.g. the types XMP-4, XMP-3, 700 C. and 237, or acid earths of the types K0 and K10 (activated with hydrochloric acid), KS and KSF (activated with sulfuric acid) or KSF0 (activated with hydrochloric acid and sulfuric acid), of Südchemie, and also earths based on bentonite, e.g. products of the types Filtrol® or Retrol®0 (Engelhard Corp.).

A particularly preferred embodiment of the process is that which comprises using Fulcat® 22 B, an acid-activated montmorrillonite containing 4% free moisture and having an acid titer of 20 mg KOH/g.

Modified sheet silicates are also called pillared clays and are derived from the above-described naturally occurring sheet silicates, containing between the silicate layers oxides of e.g. zirconium, iron, zinc, nickel, chromium, cobalt or magnesium, or elements of the rare earths. Modified sheet silicates have been described, inter alia, by J. Clark et al. in *J. Chem. Soc. Chem. Comm.* 1989, 1353–1354. Particularly preferred modified sheet silicates are, for example, the products Envirocat® EPZ-10, EPZG or EPIC produced by Contract Chemicals.

The acid catalyst can be added, for example, in an amount of 1–50, preferably of 5–25, particularly preferably of 5–20, percent by weight or, if it is a so-called Brønsted acid or Lewis acid, in an amount of 0.002 to 10 mol %, preferably of 0.1 to 5.0 mol %.

The reaction temperature in the second reaction step is from about 60° to 250° C., preferably from 110° to 200° C., particularly preferably from 160° to 195° C.

The reaction in both reaction steps can be carried out with or, preferably, without solvent or diluant. If a solvent is used, it should be inert under the given reaction conditions and should have a suitably high boiling temperature. Suitable solvents are, for example, optionally halo-genated hydrocarbons, polar aprotic solvents, liquid amides and alcohols. To be mentioned as examples are: petroleum ether fractions, preferably higher boiling ones, toluene, mesitylene, dichlorobenzene, tetrahydrofuran (THF), dimethylformamide (DMF), dimethylacetamide, (DMA), hexamethylphosphoric acid triamide (HMPTA), glymes and diglymes, dimethylsulfoxide (DMSO), tetramethylurea (TMU), alcohols, such as butanol or ethylene glycol.

The sequence of the process steps can, for example, be illustrated as follows:

Preparation of mixtures of alkylated diphenylamine and phenothiazine by reaction with diisobutylene:

Another preferred embodiment is that relating to a process for the preparation of a mixture of alkylated phenothiazines (I) and diphenylamines (II), wherein $R^1$ and $R^2$ are hydrogen, one of $R^3$ and $R^{3'}$ is hydrogen and the other is 1,4,4-trimethyl-2-pentyl or nonyl, or both $R^3$ and $R^{3'}$ are 1,4,4-trimethyl-2-pentyl or nonyl, which process comprises reacting a diphenylamine (III), wherein $R^1$ and $R^2$ are hydrogen, with elemental sulfur in the presence of iodine as condensation catalyst and reacting the obtainable substance mixture of diphenylamine (III) and phenothiazine (IV) with diisobutylene or tripropylene in situ in the presence of an acid catalyst and isolating the mixture of the compounds (I) and (II).

The mixtures of alkylated phenothiazines (I) and diphenylamines (II) obtainable according to these processes are suitable for stabilising organic compounds against light-induced, thermal and/or oxidative degradation. The mixtures

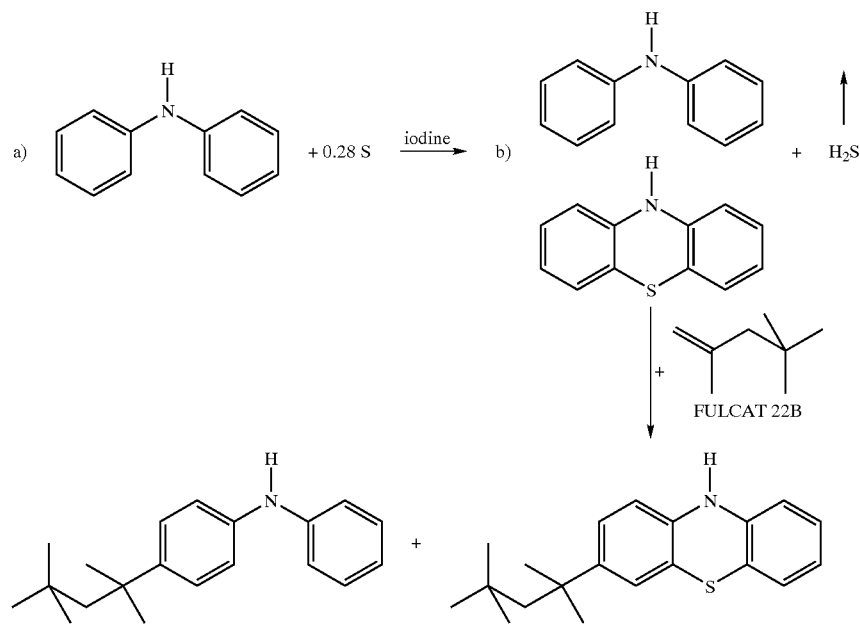

This invention preferably relates to a process for the preparation of a mixture of alkylated phenothiazines (I) and diphenylamines (II), which comprises reacting a diphenylamine (III) with elemental sulfur in the presence of a condensation catalyst selected from the group consisting of iodine, aluminium bromide, aluminium chloride, iron-III-chloride, antimonium chloride, copper iodide and sulfur iodide and reacting the obtainable substance mixture of diphenylamine (III) and phenothiazine (IV) with an olefin (V) containing the number of the carbon atoms in $R^3$ or $R^{3'}$, wherein $R^3_a$, $R^3_b$ and $R^3_c$ have the cited meanings, in situ in the presence of an acid catalyst and isolating the mixture of the compounds (I) and (II).

This invention particularly preferably relates to a process for the preparation of a mixture of alkylated phenothiazines (I) and diphenylamines (II), which comprises reacting a diphenylamine (III) with elemental sulfur in the presence of iodine as condensation catalyst and reacting the obtainable substance mixture of diphenylamine (III) and phenothiazine (IV) with an olefin (V) containing the number of the carbon atoms in $R^3$ or $R^{3'}$, wherein $R^3_a$, $R^3_b$ and $R^3_c$ have the cited meanings, in situ in the presence of an acid catalyst and isolating the mixture of the compounds (I) and (II).

can be used in particular in combination with suitable substrates as stabilisers for synthetic, semisynthetic or natural polymers, in particular thermoplastic plastic materials and elastomers, and for functional fluids, in particular lubricants, metal working and hydraulic fluids.

The cited functional fluids, e.g. lubricant compositions, such as greases, gear fluids, metal working fluids and hydraulic fluids, can additionally contain other additives which are added to further improve their basic properties. These additives include: antioxidants, metal deactivators, rust inhibitors, viscosity index improvers, stock point depressants, dispersants, detergents, high-pressure additives and antiwear additives. Such additives are added in the respective customary amounts in the range from about 0.01 to 10.0% by weight each.

The cited components can be admixed to the lubricants in a manner known per se. It is also possible to prepare a concentrate or a so-called additive blend which can be diluted in accordance with the consumption to the concentrations used for the corresponding lubricant.

Mineral and synthetic lubricating oils, lubricating greases, hydraulic fluids and elastomers thus improved have excellent antioxidant properties which show in greatly diminished signs of aging of the parts to be protected. These mixtures are particularly advantageous in lubricating oils where they show an excellent antioxidant and anticorrosive effect without any formation of acid or sludge.

The incorporation into the materials intended for the respective application can be carried out, for example, by admixing or applying the mixture obtained by these processes and optional further additives by the customary methods.

The following Examples illustrate the invention:

EXAMPLE 1

1.1. 507.7 g (3.0 mol) of diphenylamine and 26.75 g (0.834 mol) of sulfur are placed in an oil bath heated to 195° C. At an internal temperature of about 100° C., 0.1 g (0.0016 mol) of iodine is added and the temperature is raised further. After a reaction time of 15 minutes, the temperature reaches 175° C. upon which hydrogen sulfide starts to separate which is decomposed by leading in a 5% aqueous sodium hydroxide solution. The temperature is thermostatically controlled for 45 min at 185° C. A thin-layer chromatogramme (DC) shows that there is no longer any sulfur to be found in the brown reaction mixture.

1.2. The batch of process step 1.1. is allowed to cool to about 100° C. 132 g (1.176 mol) of diisobutylene and 50 g of FULCAT 22B are added and the batch is heated again in a water separator until it strongly refluxes, about 9 ml of water being separated. After a reaction time of 30 minutes, the internal temperature rises to 184° C. 396.5 g (3.534 mol) of additional diisobutylene are added dropwise such that the temperature does not fall below 165° C. (time of dropwise addition: 5½ hours). The reaction of the mixture is then allowed to go to completion under constant temperature conditions (170–175° C.) over 2 hours.

1.3. The batch is allowed to cool to about 50° C. and is then diluted with 400 ml of hexane. The catalyst is removed by filtration and the yellowish filtrate is concentrated in a rotary evaporator. The unreacted diphenylamine is distilled from the yellowish oil under vacuum at $10^{-2}$ mbar and at a bath temperature of 150° C. over 3 hours. This yields 867.3 g of a slightly yellowish brown clear oil.

Characterisation

Elemental analysis: 4.25% N; 1.29% S. Composition of the mixture in a gas chromatogramme see Table.

EXAMPLE 2

Mixtures having a higher phenothiazine content can be prepared by adding a greater amount of sulfur. The procedure is analogous to that of Example 1, using 48.1 g (1.5 mol) of sulfur. This yields 893 g of a slightly yellowish brown clear oil.

Characterisation

Elemental analysis: 4.38% N; 2.75 S%; composition of the mixture in a gas chromatogramme see Table.

EXAMPLE 3

Mixtures having a higher phenothiazine content and a higher degree of alkylation can be prepared by adding greater amounts of sulfur and by using a greater amount of diisobutylene for alkylation. The procedure is analogous to that of Example 1, using 144.3 g (4.5 mol) of sulfur and 158 g of diisobutylene. This yields 928 g of a slightly yellowish brown clear oil.

Characterisation

Elemental analysis: 4.19% N; 7.07% S; composition of the mixture in a gas chromatogramme see Table.

TABLE

Composition according to analysis by gas chromatogramme[1]

| Components in the mixture[2] | Content in percent by weight | | |
|---|---|---|---|
| | Example 1 | Example 2 | Example 3 |
| diphenylamine | 0.8 | 0.7 | 1.4 |
| phenothiazine | 0.6 | 1.7 | 3.3 |
| 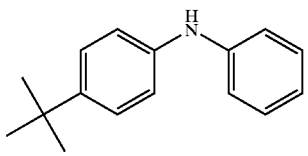 | 5.8 | 6.5 | 1.3 |
| 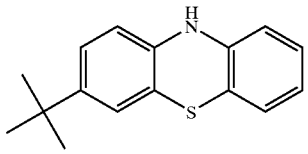 | 1.2 | 2.1 | 4.0 |
| 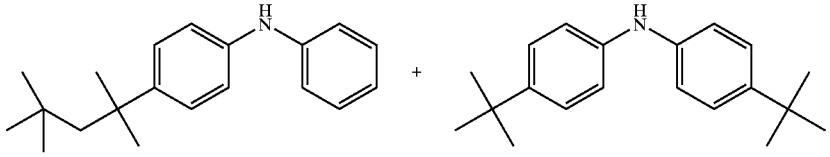 | 28.2 | 30.6 | 9.6 |

TABLE-continued

Composition according to analysis by gas chromatogramme[1]

| Components in the mixture[2] | | Content in percent by weight | | |
|---|---|---|---|---|
| | | Example 1 | Example 2 | Example 3 |
| 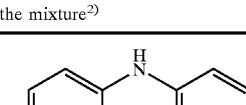 + 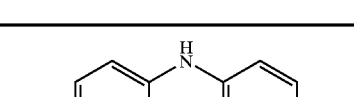 | | 5.9 | 9.4 | 26.9 |
| 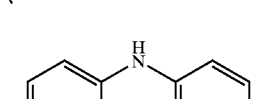 | | 15.2 | 11.1 | 3.1 |
| 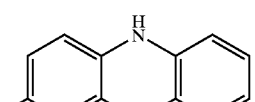 | | 2.4 | 3.7 | 10.1 |
| 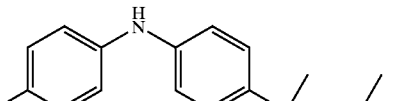 | | 33.5 | 24.1 | 10.2 |
| 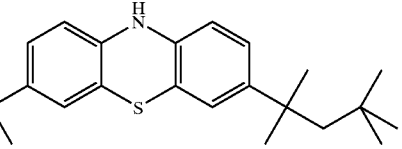 | | 5.9 | 8.1 | 30.3 |

[1])GC chromatogramme; apparatus; HP 5890, series 2; column: Macherey-Nagel, Optima-5 amine, 30 × 0.32, 1 μm.
[2])After distilling off diphenylamine

EXAMPLE 4

4.1. 338.45 g (2.0 mol) of diphenylamine and 96.2 g (3 mol) of sulfur are placed in an oil bath heated to 195° C. At an internal temperature of about 100° C., 0.1 g (0.0016 mol) of iodine is added and the temperature is raised further. After a reaction time of 40 minutes, a temperature of 175° C. is reached, upon which hydrogen sulfide starts to separate which is destroyed by leading in a 5% aqueous sodium hydroxide solution. The temperature is thermostatically controlled for 45 min at 185° C.

4.2. The batch obtained in process step 1.1. is allowed to cool to about 100° C. 250 g of tripropylene (nonene) and 35 g of FULCAT 22B are added and the batch is heated again in a water separator until it refluxes strongly, about 9 ml of water being separated. After a reaction time of 30 minutes, the internal temperature rises to 164° C. Subsequently, 760 g of tripropylene are added dropwise over 3 hours. The temperature falls to 143° C. The reaction is then allowed to go to completion under constant temperature conditions (143–145° C.) over 6 hours.

4.3. The batch is allowed to cool to about 50° C. and is then diluted with 400 ml of hexane. The catalyst is removed by filtration and the yellowish filtrate is concentrated in a rotary evaporator. The unreacted tripropylene is removed from the yellowish filtrate in a rotary evaporator. The brown oil is dried under vacuum at $10^{-2}$ mbar and at a bath temperature of 80° C. over 3 hours, yielding 721.6 g of a brown clear oil.

Characterisation

Elemental analysis: 4.28% N; 6.56% S.

What is claimed is:

1. A process for the preparation of a mixture comprising alkylated phenothiazines of formula:

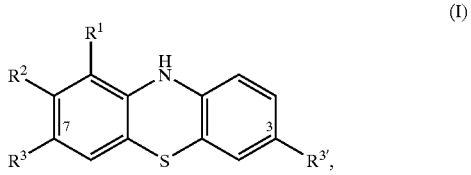

(I)

and, additionally, correspondingly substituted diphenylamines of formula:

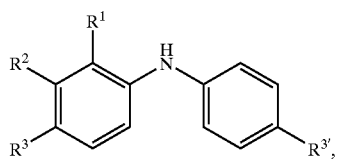
(II)

wherein $R^1$ and $R^2$ are hydrogen or together are the group:

(A)

one of $R^3$ and $R^{3'}$ is hydrogen and the other is $C_2$–$C_{30}$alkyl, cyclo-$C_5$–$C_{12}$alkyl-$C_2$–$C_4$alkyl, α-$C_1$–$C_2$alkylbenzyl or α,α-dimethylbenzyl; or both $R^3$ and $R^{3'}$ are $C_2$–$C_{30}$alkyl, cyclo-$C_5$–$C_{12}$alkyl-$C_2$–$C_4$alkyl, α-$C_1$–$C_2$alkylbenzyl or α,α-dimethylbenzyl, if $R^1$ and $R^2$ are hydrogen; or $R^3$ is hydrogen and $R^{3'}$ is $C_2$–$C_{30}$alkyl, cyclo-$C_5$–$C_{12}$alkyl-$C_2$–$C_4$alkyl, α-$C_1$–$C_2$alkylbenzyl or α,α-dimethylbenzyl, if $R^1$ and $R^2$ together are the group A, which process comprises reacting in a one pot process a diphenylamine of formula:

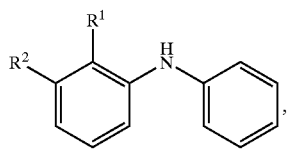
(III)

wherein $R^1$ and $R^2$ have the meanings given for formula I, with elemental sulfur in the presence of a condensation catalyst selected from the group consisting of iodine, aluminium bromide, aluminium chloride, iron-III-chloride, antimony chloride, copper iodide and sulfur iodide and reacting the resulting mixture of diphenylamine (III) and phenothiazine of formula:

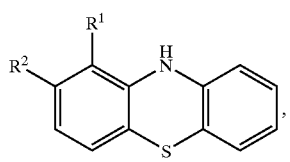
(IV)

wherein $R^1$ and $R^2$ have the meanings cited for formula I, with an olefin of formula:

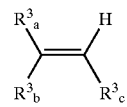
(V)

containing the number of the carbon atoms in $R^3$ or $R^{3'}$, wherein one of $R^3_a$, $R^3_b$ and $R^3_c$ is cyclo-$C_5$–$C_{12}$alkyl or phenyl and the other radicals are hydrogen or methyl, or $R^3_a$, $R^3_b$ and $R^3_c$ are each independently of one another hydrogen or $C_1$–$C_{28}$alkyl, in situ in the presence of an acid catalyst and isolating the mixture of the compounds (I) and (II).

2. A process according to claim 1 for the preparation of a mixture of alkylated phenothiazines (I) and diphenylamines (II), which comprises reacting a diphenylamine (III) with elemental sulfur in the presence of a condensation catalyst selected from the group consisting of iodine, aluminium bromide, aluminium chloride, iron-III-chloride, antimony chloride, copper iodide and sulfur iodide and reacting the resulting mixture of diphenylamine (III) and phenothiazine (IV) with an olefin (V) containing the number of the carbon atoms in $R^3$ or $R^{3'}$, wherein $R^3_a$, $R^3_b$ and $R^3_c$ have the cited meanings, in situ in the presence of an acid catalyst and isolating the mixture of the compounds (I) and (II).

3. A process according to claim 1 for the preparation of a mixture of alkylated phenothiazines (I) and diphenylamines (II), which comprises reacting a diphenylamine (III) with elemental sulfur in the presence of iodine as condensation catalyst and reacting the resulting mixture of diphenylamine (III) and phenothiazine (IV) with an olefin (V) containing the number of the carbon atoms in $R^3$ or $R^{3'}$, wherein $R^3_a$, $R^3_b$ and $R^3_c$ have the cited meanings, in situ in the presence of an acid catalyst and isolating the mixture of the compounds (I) and (II).

4. A process according to claim 1 for the preparation of a mixture of alkylated phenothiazines (I) and diphenylamines (II), wherein $R^1$ and $R^2$ are hydrogen, one of $R^3$ and $R^{3'}$ is hydrogen and the other is 1,4,4-trimethyl-2-pentyl or nonyl, or both $R^3$ and $R^{3'}$ are 1,4,4-trimethyl-2-pentyl or nonyl, which process comprises reacting a diphenylamine (III), wherein $R^1$ and $R^2$ are hydrogen, with elemental sulfur in the presence of iodine as condensation catalyst and reacting the resulting mixture of diphenylamine (III) and phenothiazine (IV) with diisobutylene or tripropylene in situ in the presence of an acid catalyst and isolating the mixture of the compounds (I) and (II).

5. A process according to claim 1 for the preparation of a mixture of alkylated phenothiazines (I) and diphenylamines (II), wherein $R^1$ and $R^2$ are hydrogen, one of $R^3$ and $R^{3'}$ is hydrogen and the other is 1,4,4-trimethyl-2-pentyl or nonyl, or both $R^3$ and $R^{3'}$ are 1,4,4-trimethyl-2-pentyl or nonyl, which process comprises reacting a diphenylamine (III), wherein $R^1$ and $R^2$ are hydrogen, with elemental sulfur in the presence of iodine as condensation catalyst and reacting the resulting mixture of diphenylamine (III) and phenothiazine (IV) with diisobutylene or tripropylene in situ in the presence of active catalysts on the basis of sheet silicates, montmorrillonites, or earths on the basis of bentonites, and isolating the mixture of the compounds (I) and (II).

* * * * *